(12) United States Patent
Sugiyama et al.

(10) Patent No.: US 9,815,384 B2
(45) Date of Patent: Nov. 14, 2017

(54) WAKEFULNESS-MAINTENANCE APPARATUS

(71) Applicants: TS TECH CO., LTD., Asaka-shi, Saitama (JP); PUBLIC UNIVERSITY CORPORATION NAGOYA CITY UNIVERSITY, Nagoya-shi, Aichi (JP)

(72) Inventors: Shinji Sugiyama, Tochigi (JP); Toyokazu Nakano, Tochigi (JP); Kiyoko Yokoyama, Nagoya (JP); Issey Takahashi, Nagoya (JP)

(73) Assignees: TS Tech Co., Ltd., Saitama (JP); Public University Corporation Nagoya City University, Aichi (JP)

( * ) Notice: Subject to any disclaimer, the term of this patent is extended or adjusted under 35 U.S.C. 154(b) by 0 days.

(21) Appl. No.: 14/413,054

(22) PCT Filed: Jul. 8, 2013

(86) PCT No.: PCT/JP2013/068685
§ 371 (c)(1),
(2) Date: Jan. 6, 2015

(87) PCT Pub. No.: WO2014/010568
PCT Pub. Date: Jan. 16, 2014

(65) Prior Publication Data
US 2015/0202991 A1  Jul. 23, 2015

(30) Foreign Application Priority Data

Jul. 9, 2012 (JP) ................................. 2012-153815

(51) Int. Cl.
*B60N 2/00* (2006.01)
*A61B 5/0245* (2006.01)
(Continued)

(52) U.S. Cl.
CPC ............ *B60N 2/002* (2013.01); *A61B 5/0051* (2013.01); *A61B 5/0245* (2013.01);
(Continued)

(58) Field of Classification Search
CPC .. B60N 2/002; B60N 2/44; B60N 2002/4485; A61B 5/0051; A61B 5/0245;
(Continued)

(56) References Cited

U.S. PATENT DOCUMENTS 5,813,989 A  9/1998 Saitoh et al.
2003/0195441 A1* 10/2003 Firouzgar ............... A61H 19/34
601/46

(Continued)

FOREIGN PATENT DOCUMENTS

JP  05-330360 A  12/1993
JP  2527730 Y2  3/1997
(Continued)

OTHER PUBLICATIONS

Extended European Search Report issued for EP 13817264.8 (May 20, 2015).

*Primary Examiner* — Zhen Y Wu
(74) *Attorney, Agent, or Firm* — Drinker Biddle & Reath LLP

(57) ABSTRACT

A wakefulness-maintenance apparatus applies a stimulus, which is not perceived to be unpleasant to most seated persons, to a seated person, and effectively maintaining the wakefulness of the seated person. After a control device provided to the wakefulness-maintenance apparatus stimulates the seated person using a first stimulus at a timing close to a human heartbeat, if an index showing the wakefulness of the seated person departs within a predetermined time from a standard indicating that the wakefulness has been maintained, the control device drives a stimulus device to (Continued)

stimulate the seated person using a second stimulus having a timing that differs from the first stimulus.

7 Claims, 11 Drawing Sheets

(51) Int. Cl.
    *A61B 5/0456*      (2006.01)
    *A61B 5/18*      (2006.01)
    *A61M 21/00*      (2006.01)
    *B60N 2/44*      (2006.01)
    *B60K 28/00*      (2006.01)
    *A61B 5/00*      (2006.01)

(52) U.S. Cl.
CPC .............. *A61B 5/0456* (2013.01); *A61B 5/18* (2013.01); *A61M 21/00* (2013.01); *B60K 28/00* (2013.01); *B60N 2/44* (2013.01); *A61B 5/6891* (2013.01); *A61B 5/6893* (2013.01); *A61B 5/742* (2013.01); *A61M 2021/005* (2013.01); *A61M 2021/0022* (2013.01); *A61M 2021/0061* (2013.01); *A61M 2021/0083* (2013.01); *A61M 2230/06* (2013.01); *A61M 2230/10* (2013.01); *A61M 2230/205* (2013.01); *A61M 2230/63* (2013.01); *B60N 2002/4485* (2013.01)

(58) Field of Classification Search
CPC ....... A61B 5/0456; A61B 5/18; A61B 5/6891; A61B 5/6893; A61B 5/742; A61M 2021/0022; A61M 2021/005; A61M 2021/0061; A61M 2021/0083; A61M 2230/06; A61M 2230/10; A61M 2230/205; A61M 2230/63; A61M 21/00; B60K 28/00

USPC ........................................................ 340/575
See application file for complete search history.

(56) References Cited

U.S. PATENT DOCUMENTS

| | | | |
|---|---|---|---|
| 2004/0201481 A1* | 10/2004 | Yoshinori | B60H 1/00 340/575 |
| 2008/0027694 A1* | 1/2008 | Gitman | A61B 5/04021 703/11 |
| 2009/0099721 A1* | 4/2009 | Imai | B60W 50/16 701/46 |
| 2010/0049066 A1 | 2/2010 | Hatakeyama | |
| 2010/0231014 A1* | 9/2010 | Gibree | B60N 2/2851 297/217.1 |
| 2010/0234741 A1* | 9/2010 | Lee | A61B 5/0205 600/484 |
| 2011/0015468 A1 | 1/2011 | Aarts et al. | |
| 2013/0331695 A1* | 12/2013 | Lee | A61B 8/543 600/438 |
| 2013/0342336 A1* | 12/2013 | Kiefer | B60W 50/14 340/436 |
| 2014/0247132 A1* | 9/2014 | Fukuma | G09G 3/14 340/815.45 |

FOREIGN PATENT DOCUMENTS

| | | |
|---|---|---|
| JP | 09-091569 A | 4/1997 |
| JP | 11-078591 A | 3/1999 |
| JP | 2012-136134 A | 7/2012 |
| WO | WO 2007/023624 A1 | 3/2007 |

* cited by examiner

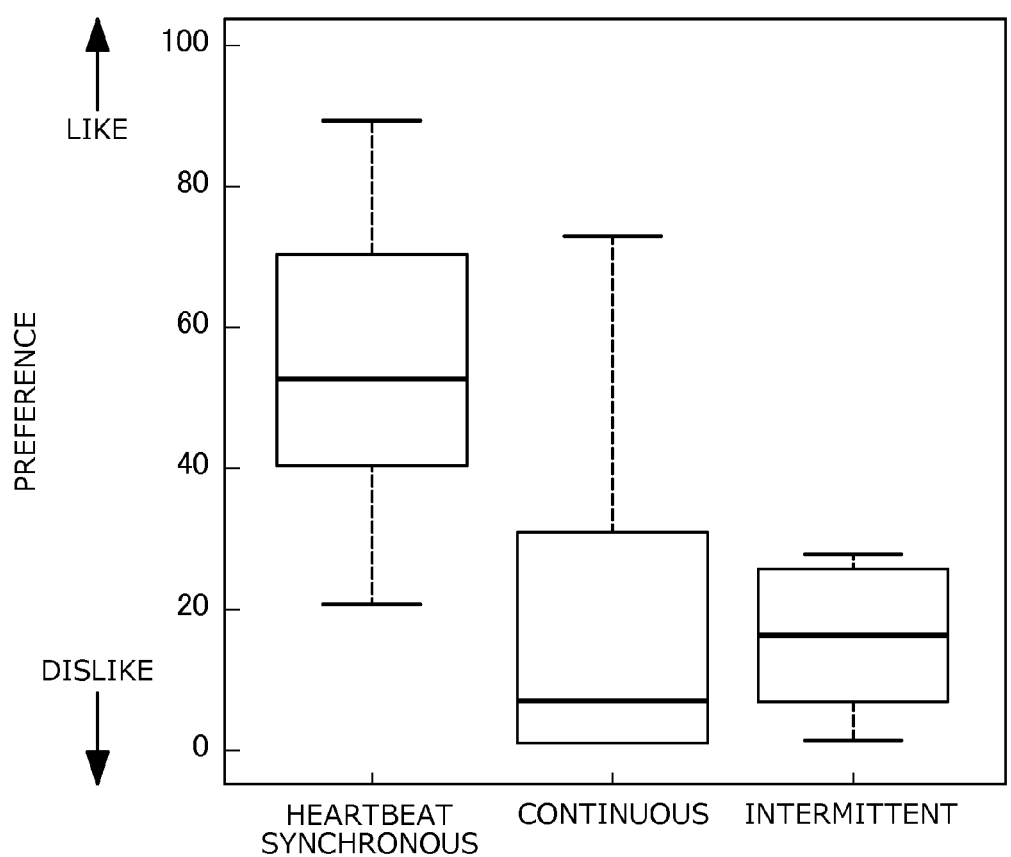

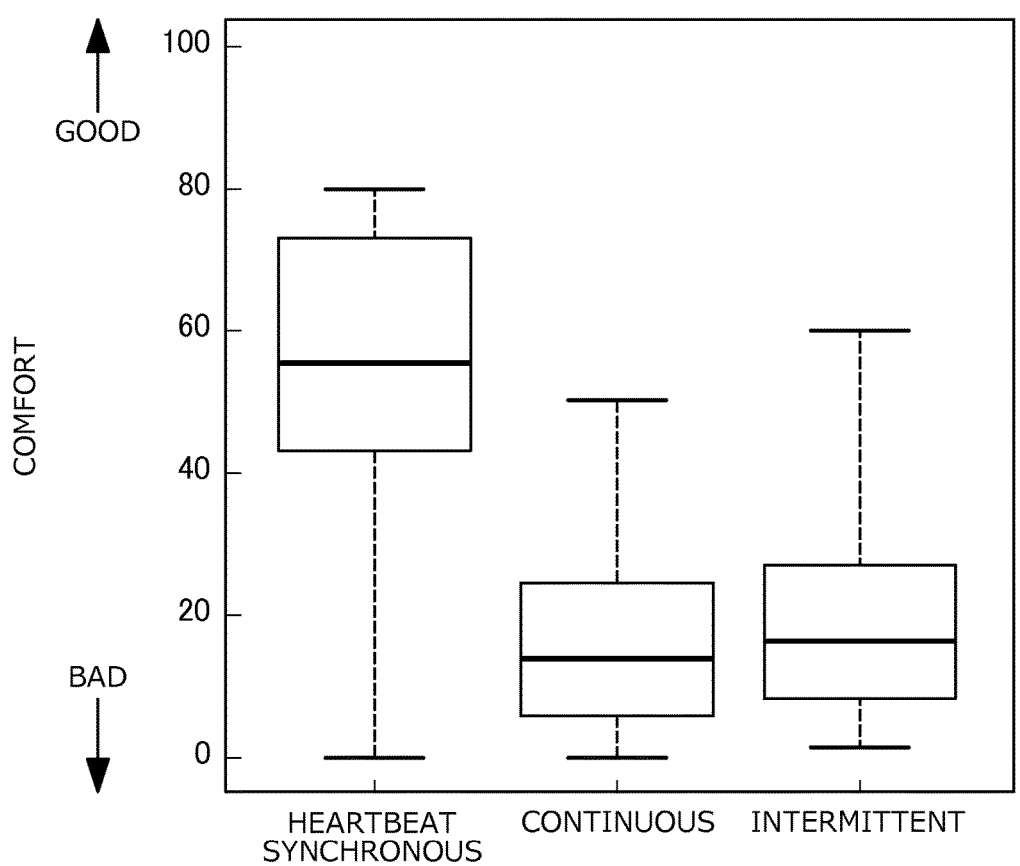

WAKEFULNESS-MAINTENANCE APPARATUS

CROSS REFERENCE TO RELATED APPLICATIONS

This application is a National Stage Entry application of PCT Application No. PCT/JP2013/068685, filed Jul. 8, 2013, which claims the priority benefit of Japanese Patent Application No. JP 2012-153815, filed Jul. 9, 2012, the contents of all being incorporated herein by reference.

BACKGROUND

Disclosed herein is a wakefulness-maintenance apparatus and, more specifically, a wakefulness-maintenance apparatus that applies a stimulus to a seated person on a vehicle seat.

Securing the safety in vehicle travel is closely related to the health condition of a driver. From this, it has been proposed that the physical condition of the driver is monitored, and the driver is called to attention by an alarm, a warning light, or the like, when an abnormal condition is detected.

For example, Japanese Patent Document No. H05-330360 A ("the '360 Document") discloses a doze prevention device that vibrates a vehicle seat at a frequency in a range which does not give discomfort to a seated person in order to prevent dozing. The frequency is specifically set to 40 Hz-50 Hz. The vibration stimulus by this device gives less unpleasant feeling and produces a wakefulness effect.

Moreover, for example, Japanese Patent Document No. H11-78591 A ("the '591 Document") discloses a device that applies a vibration stimulus having an intensity depending on the sensitivity of a seated person to the seated person by a vibrating motor if dozing of the seated person is recognized. This device produces a high wakefulness effect without being affected by the difference of the sensitivity of the seated person to the vibration stimulus.

Further, for example, Japanese Patent Document No. 2012-136134 A ("the '134 Document") discloses a device that maintains the wakefulness of a seated person without giving discomfort to the seated person by applying a vibration synchronous with the heartbeat of the seated person to the seated person.

Although there are frequencies which are perceived to be unpleasant, the device disclosed in ("the '360 Document") applies a vibration stimulus at a predefined frequency of 40 Hz-50 Hz to minimize the number of seated persons from perceiving the applied frequency as being unpleasant.

Moreover, as the device disclosed in ("the '591 Document"), even if adjustment of the vibration intensity of the vibrating motor can produce a high wakefulness effect without being affected by the difference of the sensitivity of the seated person, it has previously proven difficult to remove discomfort due to the vibration.

Moreover, as the device disclosed in ("the '134 Document"), in a case where a stimulus synchronous with the heartbeat of a seated person is applied, it is possible to prevent discomfort to the seated person. However, in a case where a similar stimulus is applied multiple times in a short time period, as represented by the drowsiness level of the seated person on vertical axis and the time on horizontal axis shown in a graph of FIG. 12, there has been a tendency that the seated person becomes accustomed to the stimulus.

Various embodiments disclosed herein consider such problems, and an object thereof is to provide a wakefulness-maintenance apparatus capable of applying a stimulus, which does not discomfort most seated persons, to a seated person, and effectively maintaining the wakefulness of the seated person.

SUMMARY

According to a wakefulness-maintenance apparatus of various embodiments, the above problems are solved by a wakefulness-maintenance apparatus including a vehicle seat having a stimulus device for stimulating a seated person, and a control device for driving the stimulus device in which, after the control device stimulates the seated person using a first stimulus at a timing close to a human heartbeat, if an index showing the wakefulness of the seated person departs within a predetermined time from a standard indicating that the wakefulness has been maintained, the control device drives the stimulus device to stimulate the seated person using a second stimulus having a timing that differs from the first stimulus.

The index showing the wakefulness level of the seated person is the time intervals of the R-wave signals, the fluctuation of the heartbeat, or the signal from a camera that monitors the behavior of the seated person's head, for example.

Moreover, if similar stimuli are applied to the seated person, the predetermined time is the time defined as a threshold between the time in which the seated person becomes accustomed to the stimulus and the time in which the seated person cannot become accustomed thereto, for example, about 30 minutes.

Thus, if the index showing the wakefulness of the seated person departs from the standard within the predetermined time after the control device applies the first stimulus at the timing close to the heartbeat of the seated person, the control device drives the stimulus device to apply the second stimulus that differs from the first stimulus to the seated person, and is thereby capable of effectively maintaining the wakefulness of the seated person by applying the first stimulus which is not uncomfortable to the seated person while preventing the seated person from being accustomed to the first stimulus.

Moreover, after the control device stimulates the seated person using the first stimulus, if the index departs from the standard after the predetermined time passes, the control device may drive the stimulus device to stimulate the seated person using the first stimulus.

Thus, after the first stimulus, if the index showing the wakefulness departs from the standard after the predetermined time in which the seated person gets accustomed thereto, the control device drives the stimulus device to stimulate the seated person using the first stimulus at the timing close to the human heartbeat, and is thereby capable of effectively maintaining the wakefulness of the seated person using a comfortable stimulus within the time in which the seated person is less likely to become accustomed to the first stimulus.

Moreover, it is preferable that the vehicle seat includes heartbeat sensors for acquiring cardiac potential signals of the seated person and the first stimulus is the stimulus synchronous with heartbeat information obtained from the cardiac potential signals.

Thus, the vehicle seat includes the heartbeat sensors, and is thereby capable of applying the stimulus synchronous with the cardiac potential signals unique to the seated person to the seated person, and effectively maintaining the wakefulness of the seated person using a comfortable stimulus.

Moreover, the second stimulus is preferably the stimulus asynchronous with the heartbeat.

Thus, the second stimulus is the stimulus asynchronous with the heartbeat, and is thereby capable of maintaining the wakefulness of the seated person being accustomed to the stimulus synchronous with the heartbeat information.

Moreover, the first stimulus may be the stimulus defined from the average heartbeat information of human and may be the predefined stimulus.

Thus, if the first stimulus is the stimulus defined from the average heartbeat information of human and is the predefined stimulus, setting and adjustment of programming to synchronize the stimulus to the heartbeat of the seated person are not necessary, and it is possible to increase production efficiency of the wakefulness-maintenance apparatus.

Moreover, the control device may drive the stimulus device to apply the second stimulus multiple times to the seated person.

Thus, if the control device drives the stimulus device to apply the second stimulus multiple times to the seated person, the wakefulness of the seated person can be realized more effectively.

Moreover, the stimulus device may be driven to stimulate the seated person depending on the detection of an R-wave in an electrocardiographic waveform according to the cardiac potential signals.

Thus, if the heartbeat sensors detect the occurrence of an R-wave of the electrocardiographic waveform, the R-wave is easily detected because of having a larger amplitude compared to other waves, e.g., Q-wave, S-wave, or the like, so that the control device can easily control the stimulus device to apply the stimulus synchronous with the heartbeat to the seated person.

Moreover, in a case where the control device cannot acquire the cardiac potential signals from the heartbeat sensors, it is preferable that the control device drives the stimulus device based on the cardiac potential signals previously acquired.

Thus, if the control device drives the stimulus device based on the cardiac potential signals previously acquired, the control device can control the stimulus device to apply the stimulus to the seated person even if the control device cannot acquire the cardiac potential signals temporarily due to the body movement or the like of the seated person.

If the index showing the wakefulness of the seated person departs from the standard within the predetermined time after the control device applies the first stimulus at the timing close to the human heartbeat to the seated person, the control device drives the stimulus device to apply the second stimulus, that differs from the first stimulus, to the seated person, and is thereby capable of effectively maintaining the wakefulness of the seated person by applying the first stimulus which is not uncomfortable while preventing the seated person from being accustomed to the first stimulus.

Moreover, after the first stimulus, if the index showing the wakefulness departs from the standard after the predetermined time in which the seated person gets accustomed thereto, the control device drives the stimulus device to stimulate the seated person using the first stimulus at the timing close to the human heartbeat, and is thereby capable of effectively maintaining the wakefulness of the seated person using a comfortable stimulus within the time in which the seated person is less likely to become accustomed to the first stimulus.

Moreover, the vehicle seat includes the heartbeat sensors, and is thereby capable of applying the stimulus synchronous with the cardiac potential signals unique to the seated person to the seated person, and effectively maintaining the wakefulness of the seated person using a comfortable stimulus.

Moreover, the second stimulus is the stimulus asynchronous with the heartbeat, and is thereby capable of maintaining the wakefulness of the seated person being accustomed to the stimulus synchronous with the heartbeat information.

Moreover, if the first stimulus is the stimulus defined from the average heartbeat information of human and is the predefined stimulus, setting and adjustment of programming to synchronize the stimulus to the heartbeat of the seated person are not necessary, and it is possible to increase production efficiency of the wakefulness-maintenance apparatus.

Moreover, if the control device drives the stimulus device to apply the second stimulus multiple times to the seated person, the wakefulness maintenance of the seated person can be realized more effectively.

Moreover, if the heartbeat sensors detect the occurrence of an R-wave of the electrocardiographic waveform, the R-wave is easily detected because of having a larger amplitude compared to other types, e.g., Q-wave, S-wave, or the like, so that the control device can easily control the stimulus device to apply the stimulus synchronous with the heartbeat to the seated person.

Moreover, if the control device drives the stimulus device based on the cardiac potential signals previously acquired, the control device can control the stimulus device to apply the stimulus to the seated person even if the cardiac potential signals cannot be temporarily acquired due to the body movement or the like of the seated person.

BRIEF DESCRIPTION OF THE DRAWINGS

FIG. 7 is a graph showing subjective evaluation of preference for the respective vibration patterns.

FIG. 8 is a graph showing subjective evaluation of comfort for the respective vibration patterns.

DETAILED DESCRIPTION

Hereinafter, embodiments of a wakefulness-maintenance apparatus according to various embodiments the present invention will be described specifically with reference to the accompanying drawings.

Figure 1:
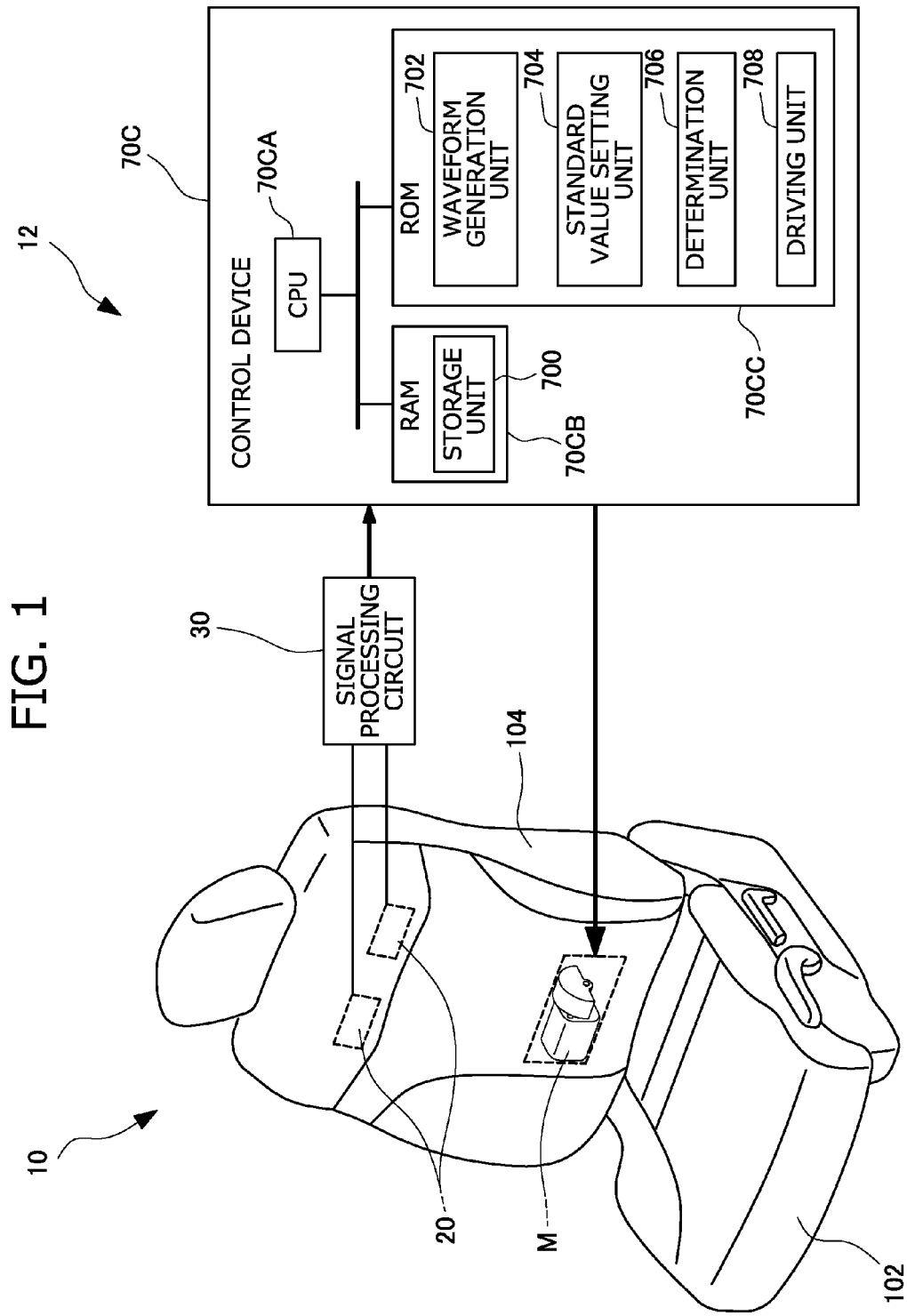
FIG. 1 is an overall pictorial block diagram showing a wakefulness-maintenance apparatus according to an embodiment of the present embodiments.

As shown in FIG. 1, a wakefulness-maintenance apparatus 12 is mainly composed of a vehicle seat 10 provided with a seat cushion 102, and a seat back 104 having heartbeat sensors 20 and a vibrating motor (stimulus device) M; a signal processing circuit 30; and a control device 70C for controlling the operation of the vibrating motor M.

The seat cushion 102 corresponds to a part where a seated person 80 is seated, and on a rear part (hereinafter, a traveling direction of a vehicle is referred to as a forward direction, and the reverse direction thereof is referred to as a rearward direction) of the seat cushion 102, the seat back 104 is rotatably attached.

Figure 2:
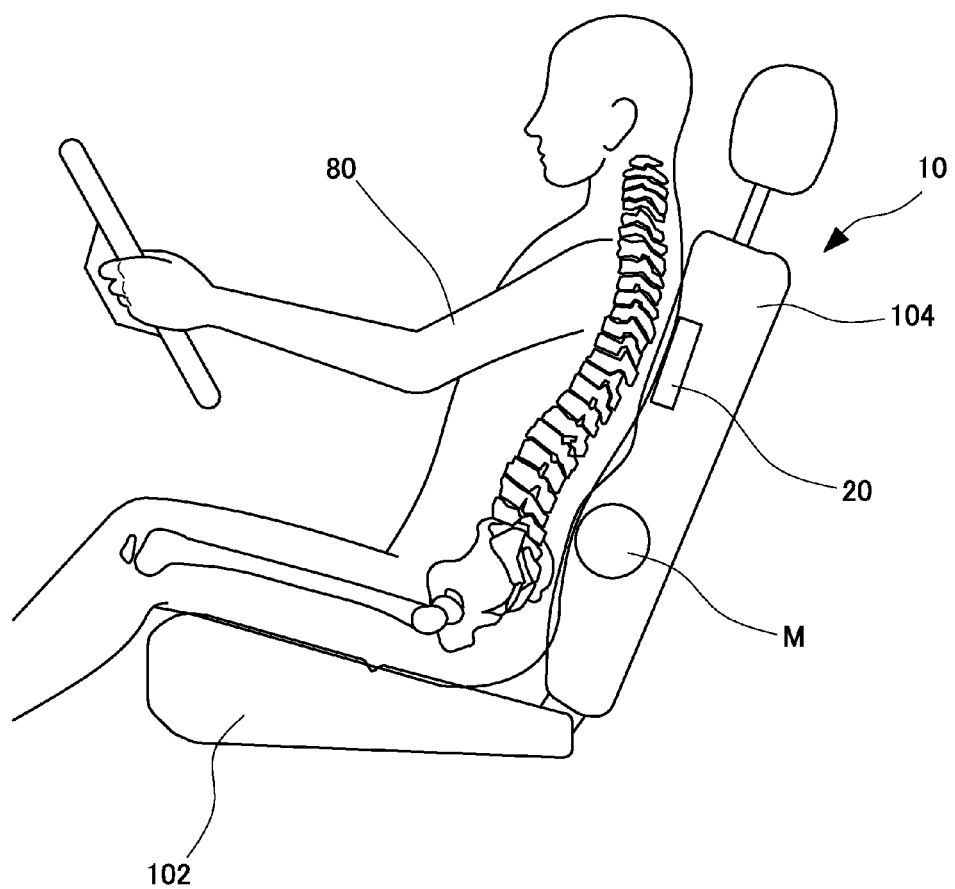
FIG. 2 is a schematic sectional side view showing a vehicle seat with a seated person.

Within the seat back 104, as shown in FIG. 2, the heartbeat sensors 20 are provided in the vicinity of a face opposed to the heart of the seated person 80, and the vibrating motor M is provided in a lower part thereof.

The heartbeat sensors 20 are electrostatic-capacitively coupled to the seated person 80 and thereby detect the physical potential, and consist of a conductive metal conductor, a conductive fiber, or a conductive fabric tape. Two heartbeat sensors 20 are horizontally arranged within the seat back 104.

The vibrating motor M consists of an unbalanced mass motor, and a rotation axis of the unbalanced mass is arranged along the width direction of the seat back 104. In operation, by arranging the vibrating motor M in this way, vertical reciprocating vibration is added to the back of the seated person 80 via the seat back 104, and a vibration stimulus is effectively applied to the seated person 80.

The signal processing circuit 30 is connected to the heartbeat sensors 20, and has a function of amplifying the physical potential detected from the heartbeat sensors 20, outputting a potential difference signal, removing noise of the potential difference signal other than an electrocardiographic frequency, and converting the potential difference signal into a digital signal.

The control device 70C has a function of drivingly controlling the vibrating motor M based on the potential difference signal converted into the digital signal, and includes a CPU (Central Processing Unit) 70CA for arithmetic control, a RAM (Random Access Memory) 70CB, and a ROM (Read Only Memory) 70CC. Moreover, the signal inputted to the control device 70C is the potential difference signal converted into the digital signal by the signal processing circuit 30, and the signal output therefrom is electric power for driving the vibrating motor M.

The RAM 70CB temporarily stores parameters including the signal under arithmetic control and the signal inputted and outputted, and has a function as a storage unit 700 for storing the potential difference signal converted into the digital signal and other signals.

The ROM 70CC stores programs to be executed by the CPU 70CA and parameters of predetermined values. In the ROM 70CC, a waveform generation unit 702 for generating electrocardiographic waveform data, a standard value setting unit 704 for setting a predetermined standard value, a determination unit 706 for determining a wakefulness state based on the standard value, and a driving unit 708 for driving the vibrating motor M are recorded as programs.

Figure 3:
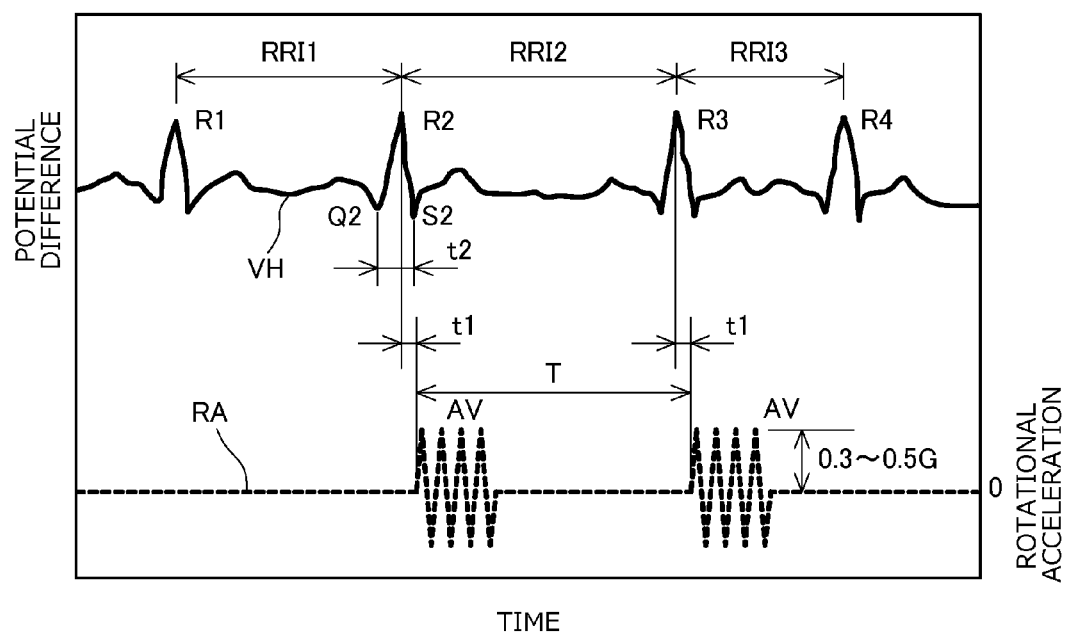
FIG. 3 is a graph showing a relationship between electrocardiographic waveform data of a seated person and a rotational acceleration of a vibrating motor.

The waveform generation unit 702 has a function of generating electrocardiographic waveform data VH with the potential difference on vertical axis and the time on horizontal axis as shown in FIG. 3, based on the potential difference signal obtained from the heartbeat sensors 20 and stored in the storage unit 700. Here, in the electrocardiographic waveform data VH in FIG. 3, R-wave signals R1, R2, R3 and R4 in the order of occurrence appear. Hereinafter, the intervals between the R-wave signals are referred to as intervals RRIs (R-R Interval), in particular, the interval between the signal R1 and the signal R2 is referred to as an interval RRI1, the interval between the signal R2 and the signal R3 is referred to as an interval RRI2, and the interval between the signal R3 and the signal R4 is referred to as an interval RRI3. Further, the interval RRI1 and the interval RRI2 are assumed to be exceeding a standard value used for determination of the wakefulness level described later, and the interval RRI3 is assumed to be not exceeding the standard value.

The standard value setting unit 704 has a function of setting a standard value serving as a standard for determination of the wakefulness state based on the electrocardiographic waveform data VH generated by the waveform generation unit 702. For example, the standard value setting unit 704 calculates an average value of a predetermined number of times of the intervals RRIs where the R-waves occur in the electrocardiographic waveform data VH previously generated, and thereafter sets a period of time of 120% of the calculated average value as a standard value.

The determination unit 706 has a function of comparing the generated electrocardiographic waveform data VH and the standard value and determining the wakefulness state of the seated person 80.

The driving unit 708 has a function of driving the vibrating motor M by supplying electric power thereto in response to an instruction of the CPU 70CA. As illustrated in FIG. 3, in a case where the interval RRI1 and the interval RRI2 are obtained in the electrocardiographic waveform data VH, the driving unit 708 rotationally drives the unbalanced mass instantaneously. Specifically, by the instantaneous rotational drive by the driving unit 708, rotation of the unbalanced mass accelerates to 0.3-0.5 G, and thereafter decelerates until the acceleration reaches −0.3-0.5 G, as shown in an acceleration waveform RA. This operation continues for approximately around 50 milliseconds, and vibration is applied to the seat back 104. Vibration waveforms AV generated by this vibration have a frequency of approximately 40 Hz. Moreover, by this drive, vibration is started in t1 seconds after the signal R2 and the signal R3 are acquired respectively. If the interval where the vibration waveforms AV are generated is referred to as an interval T, the interval T is the interval almost the same as the interval RRI2 between the signal R2 and the signal R3. That is, it is shown that the driving unit 708 drives the vibrating motor M by the vibration synchronous with the heartbeat.

First Embodiment

Figure 4:
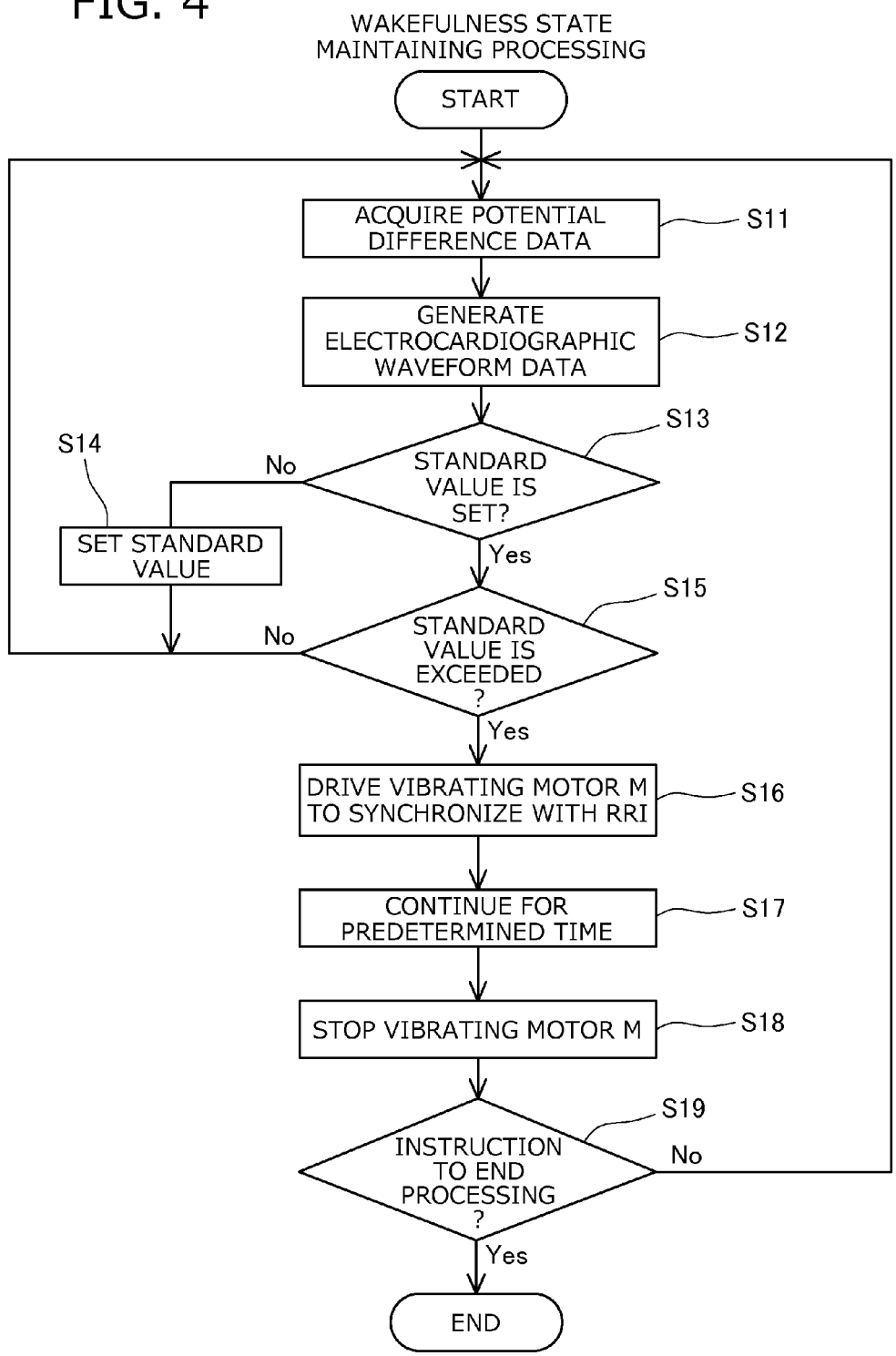
FIG. 4 is a flowchart showing a wakefulness state maintaining processing according to a first embodiment.

Next, a wakefulness state maintaining processing according to a first embodiment in which a wakefulness-reduced state is determined based on the physical potential obtained from the seated person and a stimulus synchronous with the heartbeat is applied to the seated person will be described with reference to FIG. 3 and FIG. 4.

First, the heartbeat sensors 20 detect the physical potential from the seated person 80 in response to engine start-up of the vehicle or depression of a start switch (not shown). The potential signal detected by the heartbeat sensors 20 is stored as potential difference data in the storage unit 700 of the control device 70C via the signal processing circuit 30. That is, the control device 70C acquires the potential difference data (Step S11).

Next, the waveform generation unit 702 generates the electrocardiographic waveform data VH with the potential difference and the time on axes based on the acquired potential difference data (Step S12).

Next, the CPU 70CA checks if the standard value is set (Step S13). If the standard value is not set (No in Step S13), the standard value setting unit 704 calculates an average value of a predetermined number of times of the intervals RRIs where the R-waves occur in the electrocardiographic waveform data VH, and thereafter sets a period of time of 120% of the calculated average value as a standard value (Step S14). After setting the standard value, the processing returns again to the Step S11 of acquiring the potential difference data.

If the standard value is set in Step S13 (Yes in Step S13), the determination unit 706 determines if the interval RRI of the R-wave signals in the electrocardiographic waveform data VH just before obtained exceeds the standard value (Step S15).

Moreover, in Step S15, if the determination unit 706 determines that the interval RRI just before obtained does not exceed the standard value (No in Step S15), that is, if the interval RRI3 is obtained in the electrocardiographic waveform data VH as illustrated in FIG. 3, the processing returns to Step S11 of acquiring the potential difference data without driving the vibrating motor M.

Moreover, in Step S15, if the determination unit 706 determines that the interval RRI just before obtained exceeds the standard value (Yes in Step S15), the driving unit 708 supplies electric power to the vibrating motor M, and drives the vibrating motor M by the vibration synchronous with the heartbeat signal described above, in other words, by the vibration generated in t1 seconds after the R-wave signal is obtained (Step S16).

The driving unit 708 drives the vibrating motor M to cause vibration at a vibration frequency of approximately 40 Hz, and continuously vibrates it for approximately around 50 milliseconds (Step S17). Thereafter, the driving unit 708 stops the vibrating motor M (Step S18).

Next, the CPU 70CA checks if there is an instruction to end the processing by depression of a stop switch (not shown) or the like by the seated person 80 (Step S19). If there is no instruction (No in Step S19), the processing returns to Step S11 of acquiring the potential difference data, and if there is an instruction to end the processing (Yes in Step S19), the processing ends.

Although it has been described that an average of a predetermined number of times of the R-R intervals constituting the electrocardiographic waveform data VH is calculated and 120% thereof is set as the standard value in the setting step of a standard value of Step S14, the step is not limited thereto. For example, in such a manner that a standard value is set based on the data acquired during sleep (especially at the onset of sleep) of the seated person 80, a more accurate standard value may be set. Moreover, in setting of the standard value, if the standard value can be manually set or the setting of the standard value can be changed, usability is increased.

Moreover, in determination of the determination unit 706 in Step S15, although it has been described that the standard value is compared with one R-R interval of the electrocardiographic waveform data VH just before obtained, the step is not limited thereto. In a case where reliability of determination is valued more than quickness thereof, for example, the standard value may be compared with the average of the three or four R-R intervals of the electrocardiographic waveform data VH previously obtained.

Although it has been described that the CPU 70CA performs vibration control synchronous with the heartbeat signal by performing control driving of the vibrating motor M via the driving unit 708 in such a manner that vibration is started in t1 seconds after the R-wave signal is acquired in Step S16, the step is not limited thereto. For example, period data (for example, a period of time of 120% of the average value of RRIs) synchronous with the heartbeat calculated based on the average value of a predetermined number of RRIs may be stored in the storage unit 700, and based on that data, the CPU 70CA may control the vibrating motor M to be synchronously vibrated via the driving unit 708. In this way, for example, in a case where the wakefulness level is reduced, the vibrating motor M can be driven even if R-waves cannot be acquired from the electrocardiographic waveform data VH because the heartbeat sensors 20 and the body of the seated person 80 are spaced away from each other due to the body movement or the like.

Moreover, the first stimulus which is the stimulus synchronous with the heartbeat is the stimulus defined from the average heartbeat information (the cardiac potential, pulse or the like) of human and may be the predefined stimulus. Specifically, the average heartbeat of human is 60-90 beats per minute, and the period thereof is around 667 milliseconds to 1000 milliseconds. Accordingly, the vibrating motor M may be driven to apply a stimulus to the seated person.

Moreover, the control device 70C is not limited to those performing control such that vibration is applied to the seat back 104 after a given time of t1 seconds after the R-wave signal is acquired, the timing of application of vibration may be at any point between the R-wave and the subsequent R-wave, and control may be performed to apply the vibration based on the heartbeat information. For example, the control device 70C may control the vibrating motor M to apply the vibration in such a manner that an interval from application of vibration until next application of vibration is almost the same as the detected heartbeat interval (for example, the interval from the R-wave to the subsequent R-wave).

Moreover, for example, the control device 70C may perform control to apply the vibration to the seat back 104 at a timing based on the detection of QRS-wave described later, or Q-wave, R-wave or S-wave. This timing may be set to allow a deviation of a predetermined time.

The QRS-wave means a waveform showing electrical excitation of the ventricle, which is obtained by combining the Q-wave, R-wave and S-wave. The Q-wave is a waveform which is shifted to the lower potential side than the potential (referred to as a reference potential, here) occurs when the electrical activity of the heart is in a weakened state, in the electrocardiographic waveform. Moreover, the R-wave means a waveform appearing after the Q-wave, which is shifted to the higher potential side than the reference potential. The S-wave means a waveform appearing after the R-wave, which is shifted to the lower potential side than the reference potential.

Further, it is more preferable that the vibrating motor M is vibrated during the time when the QRS-wave occurs in the electrocardiographic waveform data VH. This vibration application method will be described specifically with reference to FIG. 3. In FIG. 3, the time from the time when a Q-wave signal Q2 occurs to the time when an S-wave signal S2 occurs is referred to as t2. If the vibrating motor M is driven by control of the control device 70C so that the time when the vibration waveforms AV appear (in other words, approximately 50 milliseconds after vibration onset) overlaps with the time t2, a stimulus with lesser unpleasant feeling can be applied to the seated person 80.

The control device 70C performs such control in such a manner that, for example, the driving unit 708 drives the vibrating motor M before the signal S2 occurs in response to detection of the signal Q2 and the signal R2. In addition, the control device 70C may control the vibrating motor M to be driven during the time t2 by predicting the time when the subsequent QRS-wave occurs, based on an occurrence period and length of the previous several QRS-waves.

Quantitative Evaluation of Various Vibration Stimuli

Next, a quantitative evaluation in which three cases were compared will be described. One case is that a vibration stimulus is applied to synchronize with the heartbeat as described above (hereinafter, the stimulus by synchronous vibration is also described as a synchronous stimulus), another case is that a vibration stimulus is continuously applied regardless of the heartbeat (details thereof will be described later, and the stimulus by continuous vibration is also described as a continuous stimulus), and the other case is that a vibration stimulus is intermittently applied regardless of the heartbeat (details thereof will be described later, and the stimulus by intermittent vibration is also described as an intermittent stimulus). As an index of the quantitative evaluation, a blood oxygen saturation ($SpO_2$) in the brain of the seated person 80 was used.

Figure 5:
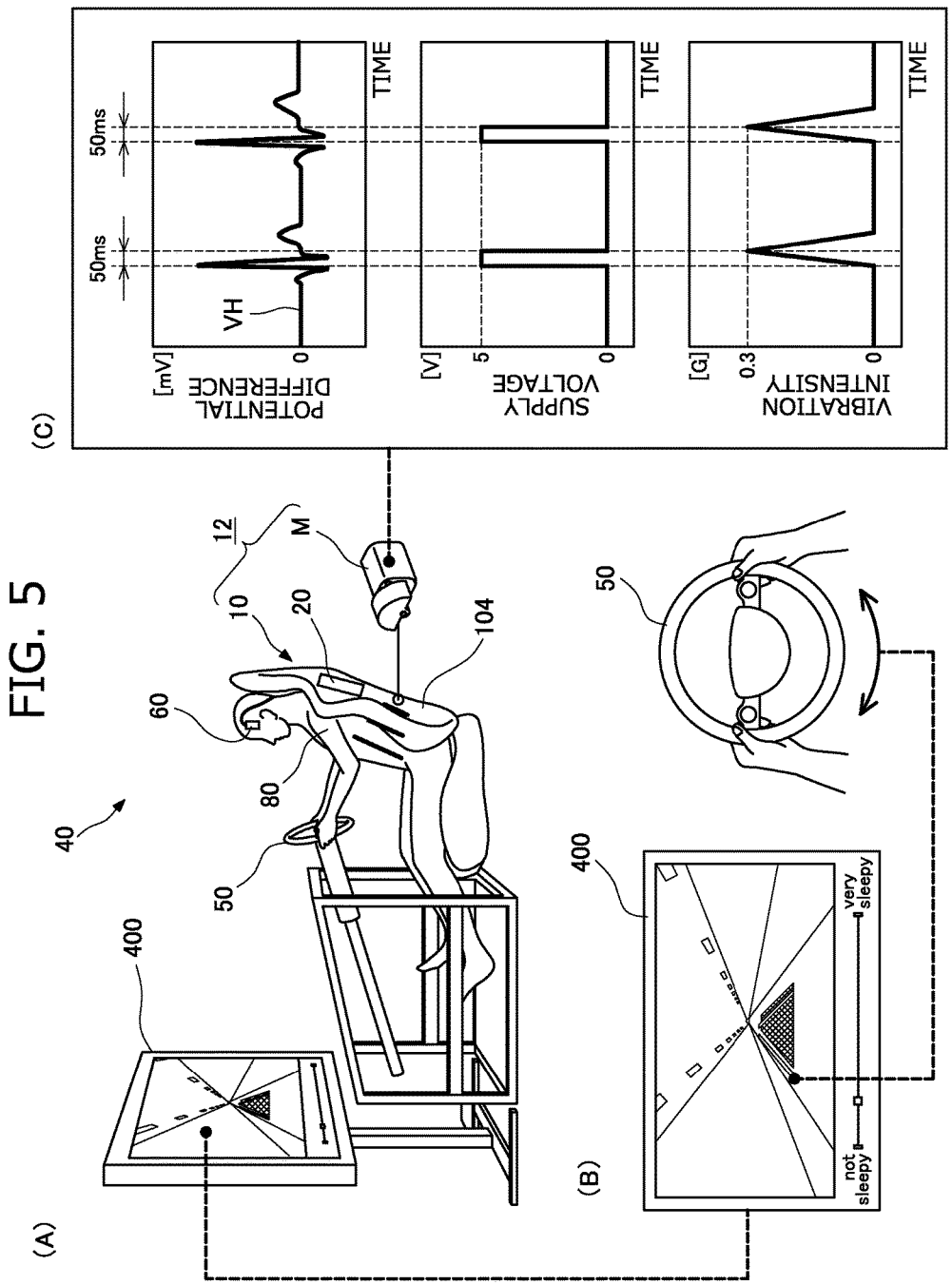
FIG. 5 is a perspective view showing a quantitative test state, connected by a leftmost dashed line to pictorial illustration showing a relationship between a display screen and manipulation, and a rightmost dashed horizontal line that are graphs showing a relationship between cardiac potential signals and timing for driving the vibrating motor.

As shown in FIG. 5 section (A) and FIG. 5 section (B), the quantitative evaluation test was conducted by the wakefulness-maintenance apparatus 12 including the vehicle seat 10 having the heartbeat sensors 20 and the vibrating motor M, the signal processing circuit 30 and the control device 70C, and a simulator 40 including an $SpO_2$ sensor 60, a monitor 400 and a steering 50.

The $SpO_2$ sensor 60 is attached to the head of the seated person 80 and detects $SpO_2$ in the brain. The monitor 400 displays a simulation video imitating the sceneries of the vehicle and during the driving thereof. The steering 50 is electrically connected to the monitor 400, and the direction of the vehicle in the simulation video is changed depending on the manipulation of the steering 50 by the seated person 80.

Application of Vibration

As shown in FIG. 5 section (C), after the R-wave is detected by the heartbeat sensors 20, a voltage of 5V is supplied to the vibrating motor M from the driving unit 708 by the CPU 70CA for approximately 50 milliseconds. Then, the vibrating motor M vibrates at a vibration intensity having a peak of 0.3 G. In this way, synchronous vibration is applied.

Figure 6:
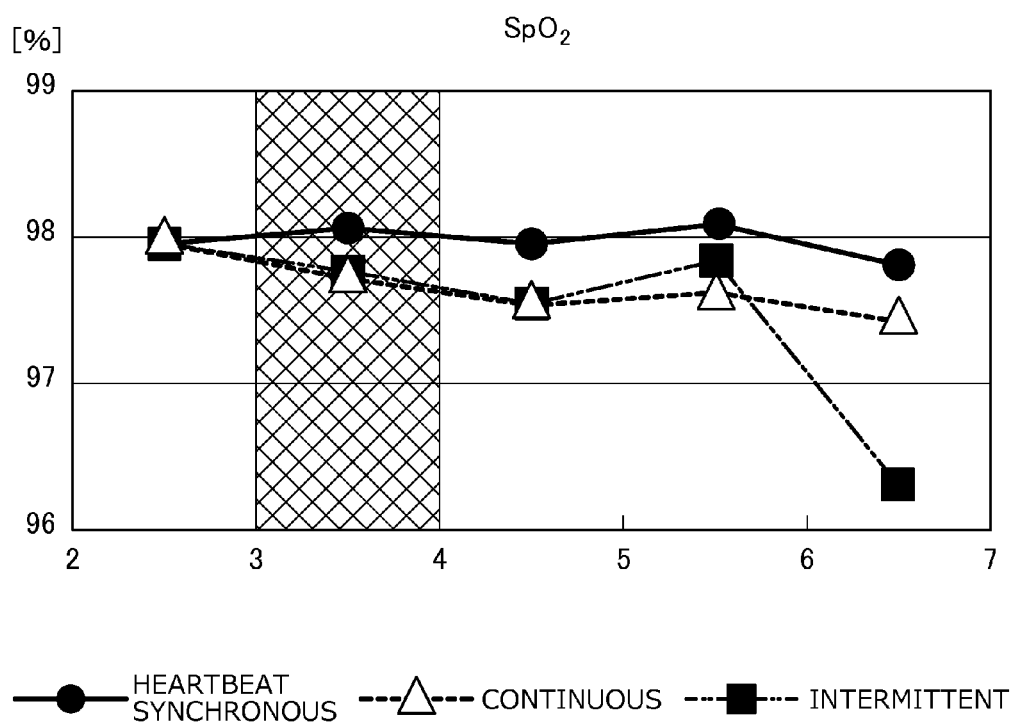
FIG. 6 is a graph showing a change of $SpO_2$ of the seated person before and after application of vibration.

FIG. 6 shows a result obtained by comparing $SpO_2$s in the respective cases where each vibration is applied. A shaded portion in FIG. 6 shows the time in which vibrations of the respective modes are applied (in the present embodiment, 3 to 4 minutes after start of measurement).

Here, the intermittent vibration whose application time and intensity are same as the above synchronous vibration is the vibration intermittently supplied to the seat back 104 from the vibrating motor M at different intervals from the vibration intervals of the synchronous vibration.

The application time and intensity of the intermittent vibration will be described specifically. As described above, the rotational speed of the unbalanced mass accelerates to 0.3-0.5 G by the instantaneous rotational drive by the driving unit 708, and thereafter decelerates at an acceleration of −0.3-0.5 G. The vibration is added to the seat back 104 by the instantaneous acceleration and deceleration of the unbalanced mass. The vibration interval of the intermittent vibration is a regular interval, and the vibration is applied at 0.5 seconds interval regardless of the heartbeat of the seated person 80. The intermittent vibration is the vibration applied to the seat back 104 by continuing this operation for approximately around 50 milliseconds. Moreover, the vibration waveforms AV generated by this vibration have a frequency of 40 Hz.

Moreover, the continuous vibration is the vibration continuously supplied to the seat back 104 from the vibrating motor M by continuously rotating the unbalanced mass of the vibrating motor M at a predetermined rotational speed.

Next, reference will be specifically made to changes before and after start of each application of stimulus. In the following description, the time before start of application of stimulus means the point of 2.5 minutes after start of measurement in FIG. 6 and the time after start of application of stimulus means the point of 3.5 minutes after start of measurement in FIG. 6.

As shown in FIG. 6, in a case where the synchronous stimulus is applied to the seated person, the values of $SpO_2$ remain almost the same before and after start of application of stimulus, and in a case where the continuous stimulus and the intermittent stimulus are applied to the seated person respectively, the values reduce in both cases after start of application of stimulus. This indicates that the synchronous stimulus maintains the wakefulness of the seated person and does not effect a specific change in a stress condition of the seated person, but that the continuous stimulus and the intermittent stimulus cannot maintain the wakefulness of the seated person and puts the seated person into a stress condition after start of application of stimulus.

Subjective Evaluation of Various Vibration Stimuli

FIG. 7 and FIG. 8 show results of subjective evaluations by a plurality of subjects whom the above synchronous stimulus, continuous stimulus and intermittent stimulus are applied. The synchronous stimulus, continuous stimulus and intermittent stimulus are described in items of "heartbeat synchronous", "continuous" and "intermittent", respectively in FIG. 7 and FIG. 8. Moreover, FIG. 7 and FIG. 8 are box plots, and, in the respective vibrations, the values on the horizontal line of the lower end are the lowest values among the values obtained from the plurality of subjects and the values on the horizontal line of the upper end are the highest values among the values obtained from the plurality of subjects. Moreover, the lower hem of the rectangle corresponds to the first quartile point, the value of bold line in the rectangle corresponds to the second quartile point (the median), and the value on the upper hem of the rectangle corresponds to the third quartile point.

The subjective evaluation produces a result that the synchronous stimulus is the stimulus preferred by persons compared to other vibration stimuli as shown in FIG. 7 and is a pleasant stimulus, in other words, the stimulus with no unpleasant feeling as shown in FIG. 8.

As described above, the wakefulness-maintenance apparatus 12 according to the present embodiment can apply a stimulus with no unpleasant feeling to the seated person 80 and maintain a wakefulness state by applying the vibration to the seated person 80 to synchronize with the heartbeat.

However, if the vibration synchronous with the heartbeat is repeatedly applied in a short time, there is a fear that the seated person becomes accustomed to the stimulus.

Thus, a wakefulness state maintaining processing according to a second embodiment capable of sustaining a wakefulness effect for a long time while preventing the seated person from being accustomed to the stimulus will be next described.

Second Embodiment

The wakefulness maintaining processing according to the second embodiment is characterized in that in addition to the stimulus synchronous with the heartbeat (described also as a synchronous stimulus or a first stimulus) described in the wakefulness maintaining processing according to the first embodiment, a stimulus not synchronous with the heartbeat (hereinafter, described also as an asynchronous stimulus or a second stimulus) is applied to the seated person.

That is, the wakefulness maintaining processing according to the second embodiment can effectively achieve wakefulness maintenance of the seated person by applying the second stimulus in addition to the first stimulus to the seated person under given conditions while preventing the seated person from being accustomed to the first stimulus.

Figure 9A:
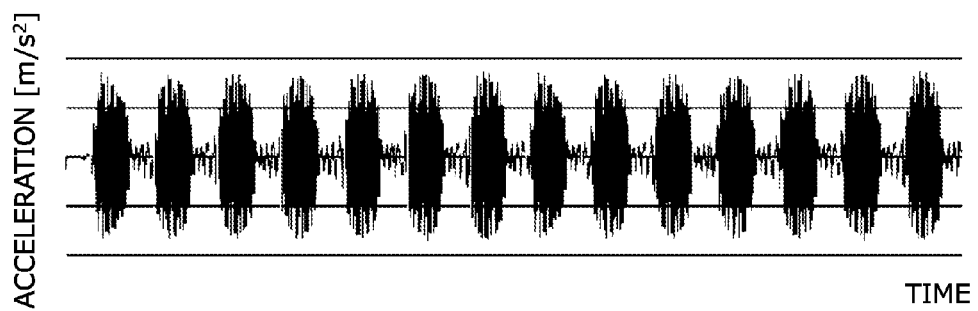
FIG. 9A is a graph showing a relationship between the time and the rotational acceleration of the vibrating motor when applying a second stimulus according to a first pattern having a timing that differs from the first stimulus.

Here, the second stimulus as an example is applied in such a manner that the increase and decrease of the rotational acceleration of the vibrating motor M are periodically performed at regular intervals in a period not synchronous with the heartbeat. In the present embodiment, the second stimulus is the stimulus in which the vibrating motor M is stopped for 100 milliseconds after vibrating it for 200 milliseconds and this operation is periodically performed, as shown in FIG. 9A.

Figure 9B:
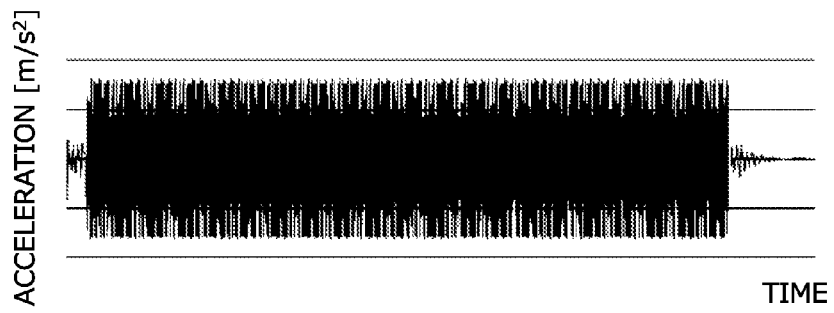
FIG. 9B is a graph showing a relationship between the time and the rotational acceleration of the vibrating motor when applying a second stimulus according to a second pattern.

Moreover, the second stimulus as another example is applied in such a manner that the increase and decrease of the rotational acceleration of the vibrating motor M are continuously performed, as shown in FIG. 9B.

In the following, the processing equal to the wakefulness maintaining processing according to the first embodiment will not be described in order to avoid repetition of description thereof.

Wakefulness State Maintaining Processing

Figure 10:
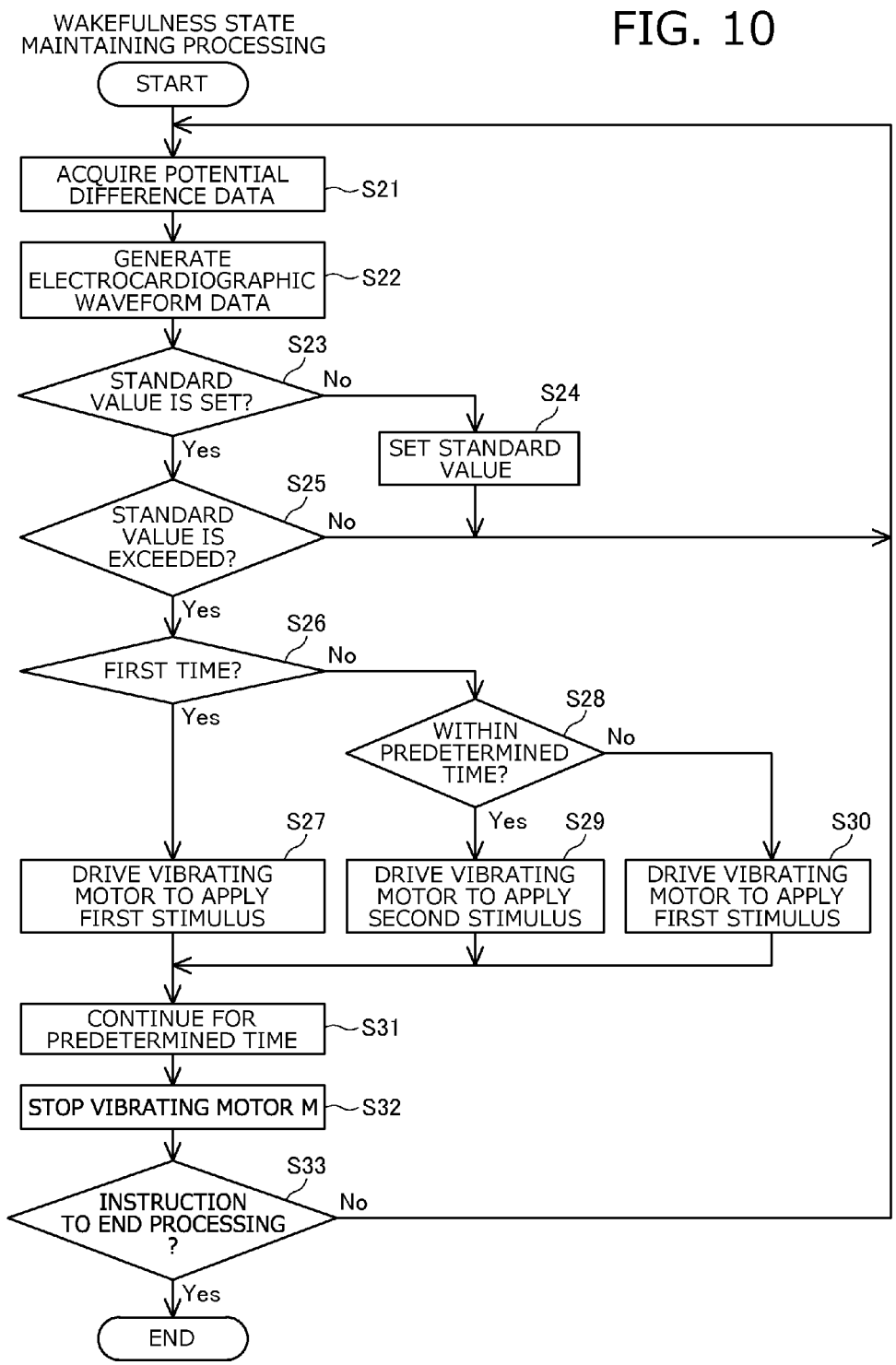
FIG. 10 is a flowchart showing a wakefulness state maintaining processing according to a second embodiment.

Next, the wakefulness state maintaining processing in which a wakefulness state is determined based on the physical potential obtained from the seated person, and the first stimulus and the second stimulus are applied according to given conditions will be described with reference to FIG. 10.

First, the heartbeat sensors 20 detect the physical potential from the seated person 80 in response to engine start-up of the vehicle or depression of a start switch (not shown). The potential signal detected by the heartbeat sensors 20 is stored as potential difference data in the storage unit 700 of the control device 70C via the signal processing circuit 30. That is, the control device 70C acquires the potential difference data (Step S21).

Next, the waveform generation unit 702 generates the electrocardiographic waveform data VH with the potential difference and the time on axes based on the acquired potential difference data (Step S22).

Next, the CPU 70CA checks if the standard value is set (Step S23). If the standard value is not set (No in Step S23), the standard value setting unit 704 calculates an average value of a predetermined number of times of the intervals RRIs where the R-waves occur in the electrocardiographic waveform data VH, and thereafter sets a period of time of 120% of the calculated average value as a standard value (Step S24). After setting the standard value, the processing returns again to the Step S21 of acquiring the potential difference data.

If the standard value is set in Step S23 (Yes in Step S23), the determination unit 706 determines if the interval RRI of the R-wave signals in the electrocardiographic waveform data VH just before obtained exceeds the standard value (Step S25).

Moreover, in Step S25, if the determination unit 706 determines that the interval RRI just before obtained does not exceed the standard value (No in Step S25), that is, if the interval RRI3 is obtained in the electrocardiographic waveform data VH as illustrated in FIG. 3, the CPU 70CA returns to Step S21 of acquiring the potential difference data without driving the vibrating motor M.

Moreover, in Step S25, if the determination unit 706 determines that the interval RRI just before obtained exceeds the standard value (Yes in Step S25), the CPU 70CA judges if the event of exceeding the standard value is the first time after start of measurement (Step S26).

If the event of exceeding the standard value is the first time (Yes in Step S26), the CPU 70CA drives the vibrating motor M by the vibration synchronous with the heartbeat signal, in other words, by the vibration generated in t1 seconds after the R-wave signal is obtained to apply the first stimulus (Step S27).

If the event of exceeding the standard value is not the first time (No in Step S26), the CPU 70CA determines if the time point of exceeding the standard value is within a predetermined time such as 30 minutes after the last application of the first stimulus (Step S28).

If the time point of exceeding the standard value is within the predetermined time after the last application of the first stimulus (Yes in Step S28), the CPU 70CA drives the vibrating motor M to apply the second stimulus which is a periodic stimulus being the asynchronous stimulus or is the continuous stimulus (Step S29).

Moreover, if the time point of exceeding the standard value this time exceeds the predetermined time after the last application of the first stimulus (No in Step S28), the CPU 70CA drives the vibrating motor M to apply the first stimulus (Step S30).

The driving unit 708 drives the vibrating motor M to apply the first stimulus or the second stimulus, and continuously vibrates it for approximately around 50 milliseconds (Step S31). Thereafter, the driving unit 708 stops the vibrating motor M (Step S32).

Next, the CPU 70CA checks if there is an instruction to end the processing by depression of a stop switch (not shown) or the like by the seated person 80 (Step S33). If there is no instruction (No in Step S33), the processing returns to Step S21 of acquiring the potential difference data, and if there is an instruction to end the processing (Yes in Step S33), the processing ends.

Figure 11:
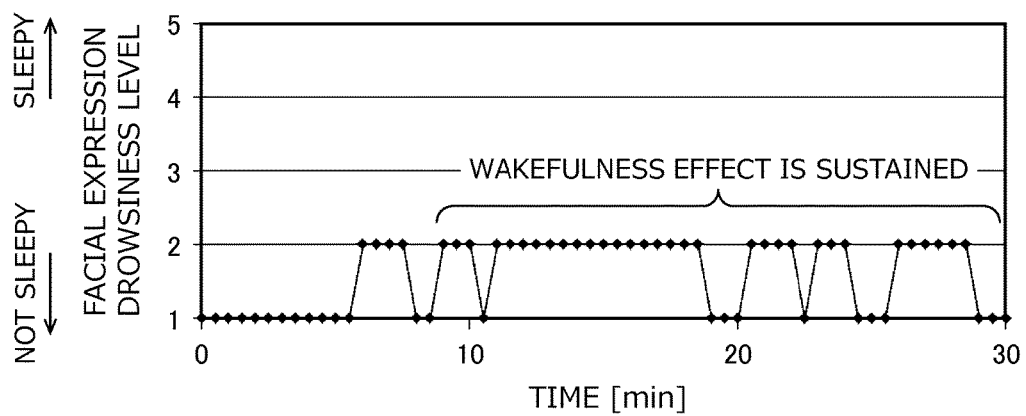
FIG. 11 is a chart showing a state that a wakefulness effect is sustained if the combination of the first stimulus and the second stimulus is applied to the seated person.
Figure 12:
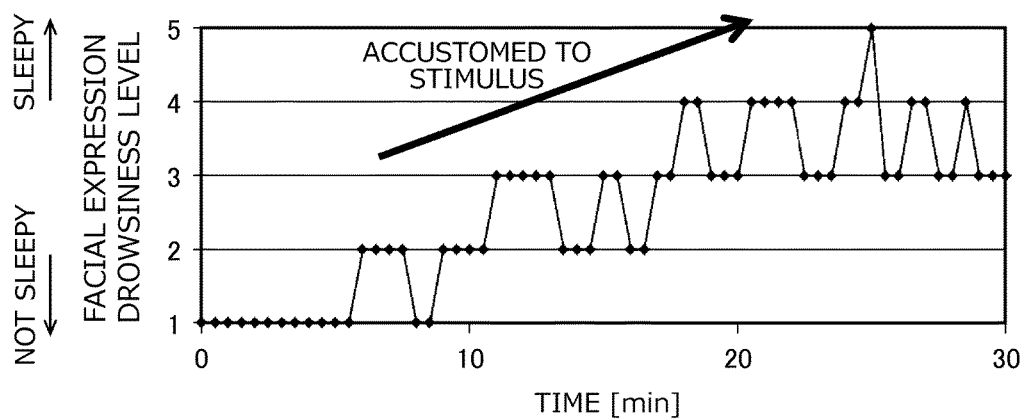
FIG. 12 is a chart showing a state that the seated person gets accustomed to the stimulus if merely the first stimulus is applied to the seated person.

Under the above conditions, by applying the synchronous stimulus and the asynchronous stimulus to the seated person, as represented by the drowsiness level of the seated person on vertical axis and the time on horizontal axis shown in a graph of FIG. 11, an effect of preventing the seated person from being accustomed to the stimuli is sustained, and an effect of maintaining the wakefulness can be provided for a long time compared to the case of applying only the synchronous stimulus shown in FIG. 12.

That is, in a case where reduction in the wakefulness state is confirmed within a predetermined time after application of the synchronous stimulus, by applying the asynchronous stimulus while preventing the synchronous stimulus from being continuously applied, the seated person can be prevented from being accustomed to the synchronous stimulus, and the wakefulness of the seated person can be maintained by the asynchronous stimulus with a strong discomfort than the synchronous stimulus for the seated person.

Further, after application of the synchronous stimulus, in a case where reduction in the wakefulness state is confirmed after the elapse of a predetermined time in which the seated person gets accustomed to the stimulus, by applying the synchronous stimulus again, the wakefulness of the seated person can be maintained using a comfortable stimulus.

Although the wakefulness-maintenance apparatuses according to various embodiments of the present invention have been specifically described, the present invention is not limited to the above embodiments. Various changes by combining the respective features and the like can be made without departing from the gist thereof.

For example, although the vibrating motor to apply the vibration stimulus by rotation of the unbalanced mass as the first stimulus or the second stimulus to be applied to the seated person has been described as an example, the present invention is not limited thereto. For example, a speaker to apply the vibration stimulus by sound waves may be used, and further, an electrode to electrically stimulate the nerves may be used. Moreover, not exclusively the vibration stimulus, a stimulus by an impact force, a stimulus by light or the like, and the like may be used.

Moreover, it is preferable that the second stimulus is applied multiple times. In particular, the second stimulus consists of a plurality of stimuli having different timings from each other, and multiple applications thereof can also prevent the seated person from being accustomed to the second stimulus due to application of the second stimulus having a single timing.

Further, the second stimulus has been described as being the stimulus in the period not synchronous with the heartbeat or the continuous stimulus. However, the second stimulus is not limited thereto, and it may be the stimulus not synchronous with the heartbeat, and may be an irregular stimulus and further the stimulus in which stimuli of the respective patterns are continuously combined.

Moreover, although a predetermined time for distinguishing application of the first stimulus from application of the second stimulus has been described above as approximately 30 minutes, it is merely illustrative. If the wakefulness maintenance of the seated person is valued, it is preferable that the cases where the predetermined time is lengthened and the second stimulus is applied are increased. Conversely, if comfort of the seated person is valued, it is preferable that the cases where the predetermined time is shortened and the first stimulus is applied are increased.

It should be noted that although the determination of the wakefulness level has been described as determination by R-R changes in the above embodiments, the wakefulness level may be determined by the fluctuation of the heartbeat (the time change of heartbeat distribution in a predetermined time), may be determined by detecting brain waves with a sensor, and may be determined based on the signal value from the camera that monitors the behavior of the head.

Moreover, although the standard value serving as a determination standard of the wakefulness state of the seated person has been described as those set based on the RRI, the standard is not limited thereto. For example, if the behavior of the head is monitored by the camera, the standard may be a predefined behavior data of the head at the onset of sleep, and the wakefulness state of the seated person may be judged depending on the degree of coincidence of the photographed behavior data of the head.

Moreover, the heartbeat information used for decision of a timing of application of vibration to the seated person is the electrocardiographic waveform data, and the determination of the wakefulness state is made using the occurrence interval of R-waves as a standard. In this manner, an acquisition system for other biological signals other than the heartbeat information is only the heartbeat sensor, and thereby, it is preferable because manufacturing cost can be reduced. However, various embodiments of the present invention may acquire and use the biological signal related to the wakefulness state, and apply the vibration to the seated person to synchronize with the heartbeat, and the biological signal acquisition means used for determination of the wakefulness state is not limited to the heartbeat sensor. For example, the determination of the wakefulness state may be made by including a sensor for acquiring respiratory signals to use a peak interval of the respiratory signals as a standard, may be made by including a sensor for detecting the pulse to use a pulse interval as a standard, and may be made by including a sensor for acquiring brain waves to use the brain waves as a standard.

REFERENCE NUMERALS

10 Vehicle seat
102 Seat cushion
104 Seat back
12 Wakefulness-maintenance apparatus
20 Heartbeat sensor
30 Signal processing circuit
40 Simulator
400 Monitor
50 Steering
60 $SpO_2$ sensor
70C Control device
700 Storage unit
702 Waveform generation unit
704 Standard value setting unit
706 Determination unit
708 Driving unit
80 Seated person
AV Vibration waveform
M Vibrating motor (Stimulus device)
RA Acceleration waveform
RRI, Interval
RRI1,
RRI2,
RRI3
T Interval
VH Electrocardiographic waveform data

The invention claimed is:

1. A wakefulness-maintenance apparatus comprising:
a vehicle seat comprising a stimulus device for stimulating a seated person; and
a control device for driving the stimulus device,
wherein:
the vehicle seat comprises heartbeat sensors for acquiring cardiac potential signals of the seated person, and
the control device:
drives the stimulus device to stimulate the seated person using a first stimulus synchronous with a human heartbeat during the time when a QRS-wave occurs in an electrocardiographic waveform according to the cardiac potential signals, if an index showing wakefulness of the seated person departs from a standard value indicating that the wakefulness has been maintained, and drives the stimulus device to stimulate the seated person using a second stimulus having a timing that differs from the first stimulus, if the index showing wakefulness of the seated person departs from the standard value within a predetermined time after driving the stimulus device to stimulate the seated person using the first stimulus.

2. The wakefulness-maintenance apparatus according to claim 1, wherein after the control device stimulates the seated person using the first stimulus, if the index departs from the standard value after the predetermined time passes, the control device drives the stimulus device to stimulate the seated person using the first stimulus.

3. The wakefulness-maintenance apparatus according to claim 1, wherein the second stimulus is a stimulus asynchronous with the heartbeat.

4. The wakefulness-maintenance apparatus according to claim 1, wherein the first stimulus is a stimulus defined from an average heartbeat information of a human and is a predefined stimulus.

5. The wakefulness-maintenance apparatus according to claim 1, wherein the control device drives the stimulus device to apply the second stimulus multiple times to the seated person.

6. The wakefulness-maintenance apparatus according to claim 1, wherein the control device drives the stimulus device to stimulate the seated person depending on a detection of an R-wave in the electrocardiographic waveform according to the cardiac potential signals.

7. The wakefulness-maintenance apparatus according to claim 1, wherein, in a case where the control device cannot acquire the cardiac potential signals from the heartbeat sensors, the control device drives the stimulus device based on the cardiac potential signals previously acquired.

* * * * *